United States Patent
Beyeler

(10) Patent No.: US 11,425,943 B2
(45) Date of Patent: Aug. 30, 2022

(54) COOLING SUIT

(71) Applicant: Patrick G. Beyeler, Arzier le Muids (CH)

(72) Inventor: Patrick G. Beyeler, Arzier le Muids (CH)

(73) Assignee: Patrick G. Beyeler, Arzier le Muids (CH)

( * ) Notice: Subject to any disclaimer, the term of this patent is extended or adjusted under 35 U.S.C. 154(b) by 185 days.

(21) Appl. No.: 15/747,108

(22) PCT Filed: Jul. 12, 2016

(86) PCT No.: PCT/EP2016/066485
§ 371 (c)(1),
(2) Date: Jan. 23, 2018

(87) PCT Pub. No.: WO2017/012908
PCT Pub. Date: Jan. 26, 2017

(65) Prior Publication Data
US 2018/0213855 A1 Aug. 2, 2018

(30) Foreign Application Priority Data

Jul. 23, 2015 (CH) .................................. 01075/15

(51) Int. Cl.
*A41D 13/005* (2006.01)
*A41D 27/28* (2006.01)
(Continued)

(52) U.S. Cl.
CPC ..... *A41D 13/0053* (2013.01); *A41D 13/0025* (2013.01); *A41D 13/02* (2013.01);
(Continued)

(58) Field of Classification Search
CPC .............. A41D 13/002; A41D 13/0025; A41D 13/0053; A41D 13/02; A41D 27/02;
(Continued)

(56) References Cited

U.S. PATENT DOCUMENTS 2,573,414 A 10/1951 Dunn
2,657,396 A * 11/1953 Klein ................. A41D 13/0025
4/536
(Continued)

FOREIGN PATENT DOCUMENTS

DE 1822905 U 12/1960

OTHER PUBLICATIONS

International Search Report; PCT Application No. PCT/EP2016/066485; dated Jan. 26, 2017.
(Continued)

*Primary Examiner* — Kaitlyn E Smith
*Assistant Examiner* — Bradford C. Blaise
(74) *Attorney, Agent, or Firm* — Polsinelli PC

(57) ABSTRACT

Cooling suit including legs, torso and arms, which includes outwardly opening hose sleeve in the hip area, inwardly branching gas ducts having several outlet openings. A pressurized gas cylinder for carrying along and connecting outlet hose with coupling piece to this hose sleeve, and which comprises a valve and adjusting wheel for the regulated delivery of expanded gas into these gas ducts. The gas ducts in the upper-body have outflow openings in the area of the lower back, hips, neck area, armpits, arm joints, and sleeves. In the lower-body garment, outflow openings are arranged in the knees and the crotch area. This cooling suit is operated with a dry, compressed gas. The gas flowing from the pressure cylinder is expanded, subsequently cools down and then flows through the gas ducts and cools the body. Perspiration is carried away by the permanent gas supply via the breathable fabric of the suit.

3 Claims, 3 Drawing Sheets

(51) Int. Cl.
*A41D 13/002* (2006.01)
*A62B 17/00* (2006.01)
*A41D 27/02* (2006.01)
*B32B 3/20* (2006.01)
*A61F 7/00* (2006.01)
*A41D 13/02* (2006.01)

(52) U.S. Cl.
CPC ............ *A41D 27/02* (2013.01); *A41D 27/28* (2013.01); *A62B 17/005* (2013.01); *B32B 3/20* (2013.01); *A41D 2300/322* (2013.01); *A61F 2007/0063* (2013.01); *A61F 2007/0064* (2013.01); *B32B 2307/724* (2013.01); *B32B 2437/00* (2013.01)

(58) Field of Classification Search
CPC ............ A41D 27/28; A41D 2300/322; A62B 17/005; B32B 3/20; B32B 2307/724; B32B 2437/00
See application file for complete search history.

(56) References Cited

U.S. PATENT DOCUMENTS

| | | | | |
|---|---|---|---|---|
| 3,738,367 | A * | 6/1973 | Hardy | A61F 7/02 607/104 |
| 4,738,119 | A | 4/1988 | Zafred | |
| 5,970,519 | A * | 10/1999 | Weber | A41D 13/0025 2/102 |
| 6,109,338 | A * | 8/2000 | Butzer | A41D 13/005 165/46 |
| 6,209,144 | B1 * | 4/2001 | Carter | A62B 17/005 2/458 |
| 6,901,608 | B2 * | 6/2005 | Szczesuil | A41D 13/005 2/458 |
| 6,957,697 | B2 * | 10/2005 | Chambers | A41D 13/005 165/297 |
| 7,089,995 | B2 * | 8/2006 | Koscheyev | A41D 13/005 165/46 |
| 7,527,612 | B1 | 5/2009 | Carpenter | |
| 7,674,281 | B2 * | 3/2010 | Worm | A62B 17/005 128/201.29 |
| 7,716,940 | B2 | 5/2010 | Franworth et al. | |
| 7,827,624 | B1 * | 11/2010 | Cole | A41D 13/0025 2/102 |
| 2004/0000343 | A1 * | 1/2004 | Turan, Jr. | B25F 5/00 137/561 R |
| 2006/0174392 | A1 | 8/2006 | Farnworth et al. | |

OTHER PUBLICATIONS

English Translation of International Search Report; PCT Application No. PCT/EP2016/066485; dated Jan. 26, 2017.
Written Opinion of PCT Application No. PCT/EP2016/066485; dated Jan. 26, 2017.
English Description of DE1822905; Retreived From www.espacenet.com on Jan. 22, 2018.

* cited by examiner

COOLING SUIT

CROSS-REFERENCE TO RELATED APPLICATIONS

This application is a national stage entry of PCT/EP2016/066485 filed Jul. 12, 2016, which claims convention priority from Swiss patent application 01075/15 filed on Jul. 23, 2015, the contents each of which are hereby incorporated by reference in their entirety.

FIELD

The present invention relates to a suit for cooling the body for working and for leisure activities in high outside temperatures and/or in high humidity, i.e. in humid and muggy weather.

BACKGROUND

Many activities in the professional world as well as in armies and security forces are carried out under difficult conditions, especially at elevated outside temperatures and/or high humidity. Performing work at high outside temperatures, in particular if additionally the humidity is high, strikingly reduces the efficiency. Construction workers on construction sites in hot climates are exhausted after a short time. Firefighters who are in service in the event of fires or rescue forces who have to intervene in hot zones during disaster suffer from the great heat and soon reach the limits of their capabilities. Another example are pilots and crews of jet-powered fighter aircraft during the preparation and post-flight phases. They often wait in standby mode or perform preparatory work outside the aircraft until they are able to enjoy the on-board air-conditioning system of the aircraft. In order to quickly be deployable, however, they are already wearing the operational clothing, i.e. full flight suit and/or combat outfit. This is heavy and hardly allows for body breathing. One quickly starts to sweat and long periods outdoors at high outside temperatures and/or high humidity become torture. However, pilots and crew members of helicopters and other transport and special aircraft are also often exposed to high temperatures and/or high humidity during the pre-flight and post-flight phases while having to wear their special operational clothing, which is predestined to cause heat accumulation. This is particularly true during extreme operations, when the aircraft and their air-conditioned cabins—if they are air-conditioned at all—have to be left. However, not only aircraft crews but also those of ships and land vehicles operating on special missions in hot climates are confronted with the problem of high temperatures and/or high humidity. In principle, their performance is markedly reduced at high prevailing temperatures and/or high humidity.

Specifically specialists of the fire services, dangerous-goods squads or special units who are deployed for example to defuse unexploded ordnance and explosive devices suffer particularly when the outside temperatures and/or humidity are high while they have to work under full protection with special protective clothing. However, also professional groups working under extreme conditions, such as tunnel builders, miners or foundrymen in the area of blast furnaces, or workers at oil wells in hot desert areas or on drilling platforms in hot climates, are exposed to high temperatures and often humid air and are correspondingly strained. The same applies to all agricultural and forestry workers and seafarers who must perform work outdoors or in rooms and areas of elevated temperature and/or humidity. Their performance and well-being are directly dependent on the prevailing temperature and current humidity. After all, this problem also affects recreational activities. Gardening in hot and/or humid weather is very strenuous and tiring, yet also outdoor sports activities such as walks, hikes, running, ball games and cycling can become torture or are often omitted when the weather is too hot or humid.

Up to now, there are no convincing solutions for cooling the worker staff and operational personnel when it has to be active in hot ambient temperature and/or high humidity. The known proposals usually include electrically powered cooling systems, such as protective suits with built-in miniature electric fans, or wetsuits with liquid cooling, wherein the cool liquid circulates through ducts in the suit and flows externally via a circuit through a cooling equipment and is cooled therein. For its operation, this depends on electrical current or at least on an combustion engine. This solution therefore requires a permanent hose connection to such a relatively heavy external unit.

The known solutions are all hardly practicable, cumbersome to use and elaborate. They include many components, some of which are heavy and require an external energy source for their use. Furthermore, the many components are reflected in the high purchase costs of such a cooling suit. Operating and handling these cooling suits can moreover not be described as particularly easy.

In view of this situation, it is the object of the present invention to create a cooling suit for anyone who wants to or must work or be active in hot ambient air and/or high humidity, wherein this cooling suit should be light, efficient, easy to use, inexpensive to purchase and maintain, and foolproof in its operation.

This object is solved by a cooling suit consisting of a suit for legs, torso and arms, which includes, starting from an outwardly opening hose sleeve, inwardly branching gas ducts having several outlet openings, as well as a respective pressurized gas cylinder for carrying along, or a corresponding stationary pressure vessel for connecting an outlet hose with coupling piece to the hose sleeve, wherein a valve with an adjusting wheel is provided at the pressurized gas cylinder or at the suit for the regulated delivery of expanded gas from the pressurized gas cylinder or the stationary pressure container into these gas ducts.

In contrast to all currently available air-powered body cooling systems, which use warm and/or humid air drawn in from the environment, this cooling suit is operated with a dry, compressed gas carried along in a pressurized gas cylinder. Strategically placed flat gas ducts direct the dry and expanded and thus cold gas to the various distinct sweating body locations, resulting in an efficient and physiologically compatible cooling effect. Cooling by natural convection is supported by the system and sweat on the surface is transported away by the permanent supply of gas via the breathable fabric.

BRIEF DESCRIPTION OF THE DRAWINGS

This cooling suit is shown as an example on the basis of the drawings and is described below. Its function and handling is explained and illustrated. There are shown.

DETAILED DESCRIPTION

Figure 1:
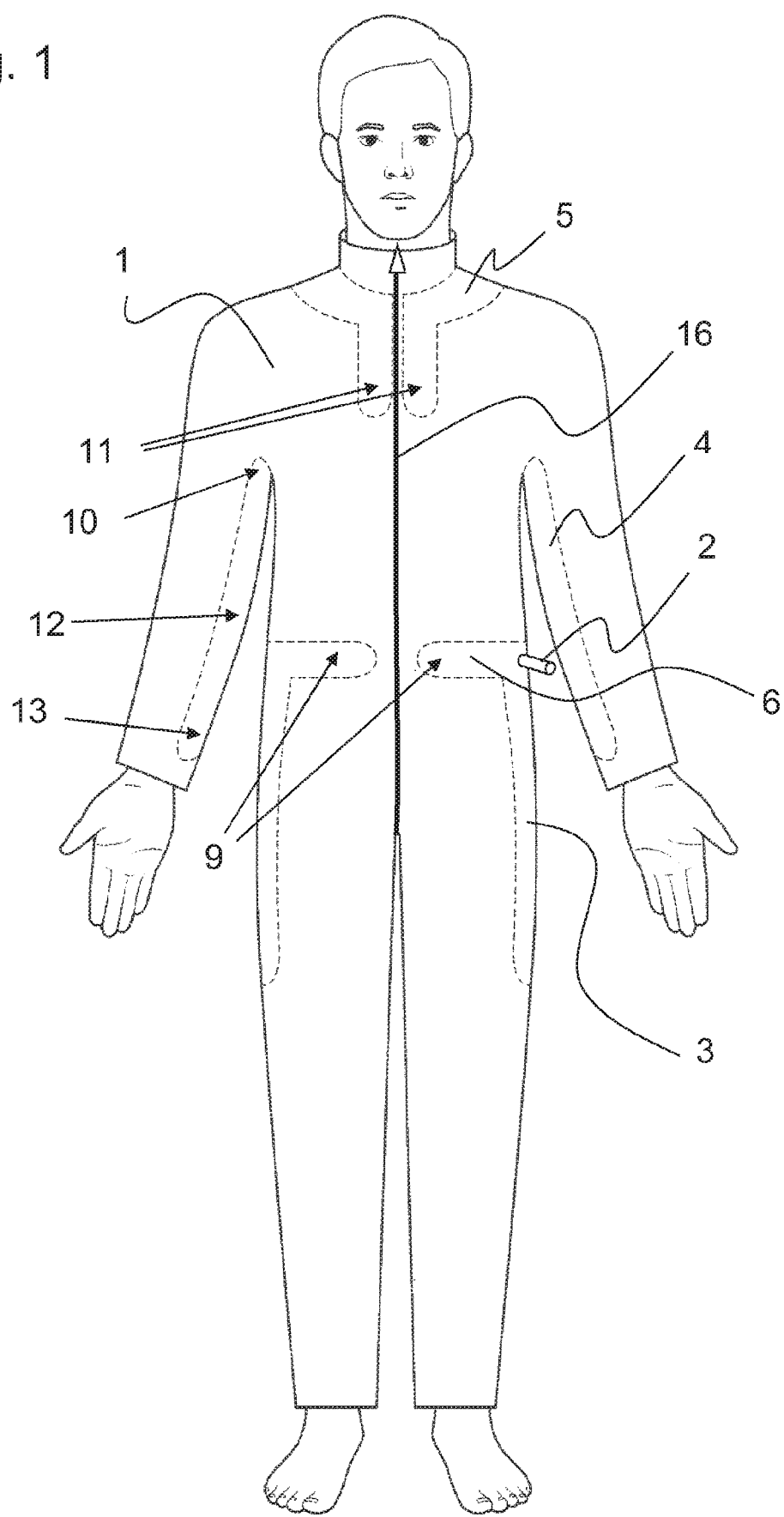
FIG. 1: A wearer of the cooling suit seen from the front, with the flat gas ducts arranged on the inner side of the outer skin of the cooling suit, which are drawn as dashes because they are not visible from the outside.

The cooling suit is shown in FIG. 1 on a carrier, wherein this is pictured as seen from the front. The cooling suit is a textile suit, shown here in the form of a so-called combination suit 1, i.e. in one part having trouser legs and an upper-body garment for torso and arms. The suit 1 is equipped with a zip fastener 16, which extends from the crotch to the top of the collar for easily putting on and taking off the suit. As a special feature, this suit 1 is equipped with different gas ducts 3-6 on the inner side of its outer layer. Here, their course is drawn as dashes because these gas ducts 3-6 are not visible from outside. These gas ducts 3-6 are designed, for example, as flat textile ducts, which are provided inside or outside with a gas-impermeable layer and which are attached to the inner side of the suit 1 by laminating, welding, or are stitched to the inner side of the suit 1 or sewn on the inner side.

In the example shown, these gas ducts 3-6 start as a branching duct system with a hose sleeve 2 with coupling protruding laterally from the suit 1 in the hip area. It is meanwhile clear that this hose sleeve could also protrude from the suit elsewhere, for example in the chest area. From the hose sleeve, a gas channel 6 leads into a ring which encloses the hip, wherein the ring in the front area is left open for opening the zip fastener 16. Starting from this ring, one gas channel 3 each branches down from the hip area and is led downward somewhat on the outer side of the trouser leg for the thigh and leads further down to the back side of the trouser leg to finally end in the area of the hollow of the knee.

Figure 2:
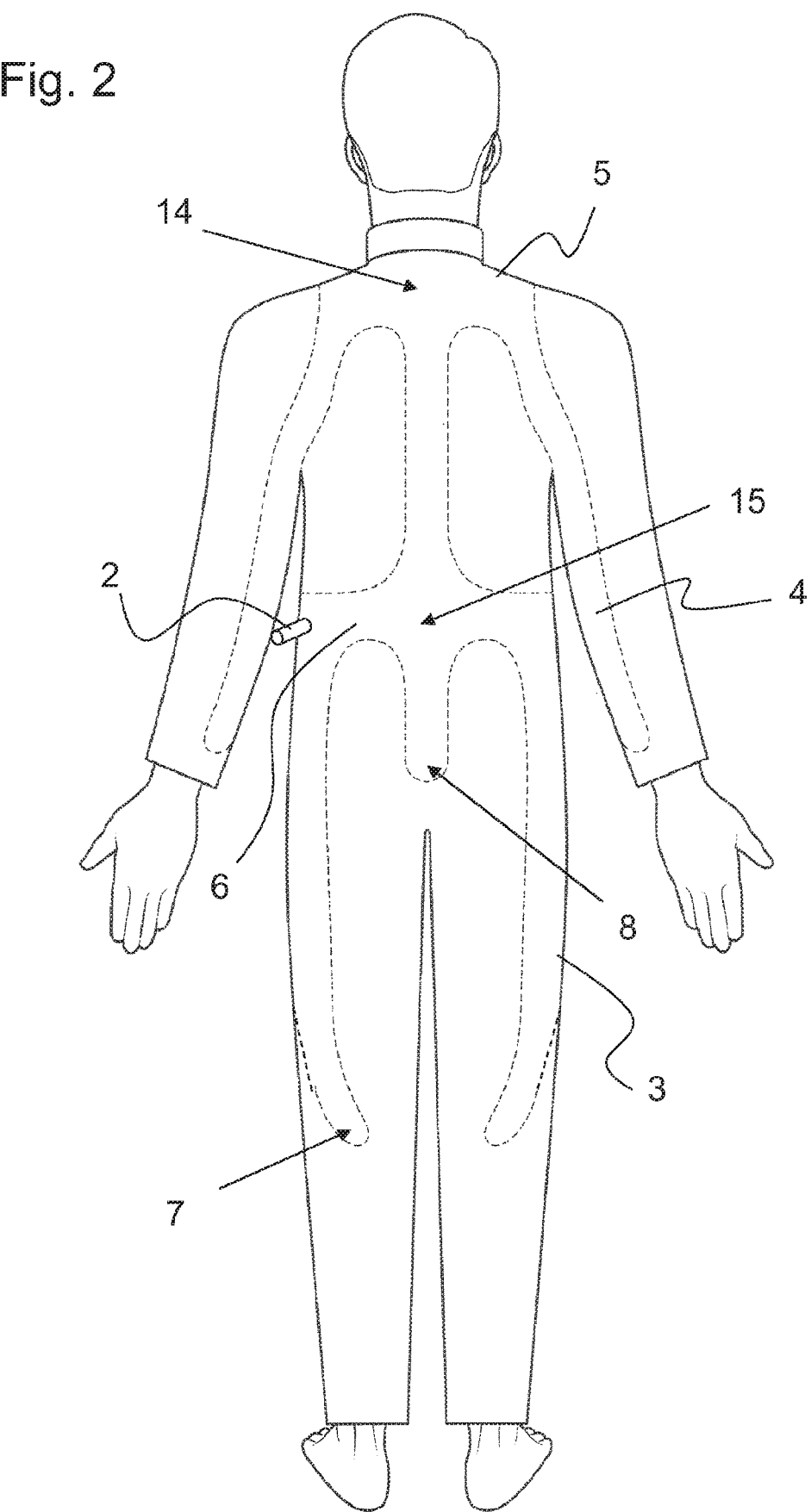
FIG. 2: the wearer of the cooling suit according to FIG. 1 seen from behind, with the flat gas ducts arranged on the inner side of the outer skin of the cooling suit, which are drawn in dashed lines because they are not visible from the outside.

The further course of the gas ducts is revealed with the aid of FIG. 2, which shows this wearer of the cooling suit as seen from behind in FIG. 1. From the ring which surrounds the hip, a gas channel from the area of the lower back 15 branches upward and runs along the spine into another ring-shaped gas channel 5, which surrounds the neck and throat of the wearer. This ring is also open at the front, as can be seen in FIG. 1 so that the full-length zip fastener 16 can be opened. Starting from the ring, two sections run down the front of the suit along the zip fastener 16 and end in the chest area 11 of the wearer. Starting from the ring-shaped gas channel 5, a gas channel 4 branches off over the shoulders into the sleeves of the suit. These two gas channels 4 run along the sleeves, preferably on that side of the sleeves facing the inner side of the arms of the wearer. Finally, there is a gas channel which at the hip branches off at the rear from the ring downwardly in the middle, which leads downward into the buttocks area and ends in the area of the crotch 8.

These different gas ducts 3-6 are all supplied by the hose sleeve 2 and by a connected hose from a pressurized gas cylinder with the expanded gas drawn from it, as this becomes clear later on the basis of FIG. 3. The gas cooled down by the expansion, in the simplest case ordinary air, flows from the hose sleeve 2 into the entire branching gas duct system and is led to respectively flow out at certain points, wherein the remaining gas continues to flow in the duct system. These outflow points are marked with arrows in FIGS. 1 and 2. These are the places where the body transpires primarily and where it can efficiently dissipate the heat. A first outlet opening is located in the area of the lower back 15 of the wearer and on the front side of the ring surrounding the hip in the area of the abdomen 9. The next outlet opening is in the area of the next 14 and in the area of the chest 11. The gas or air ducts 4, which are led via the shoulders into the sleeves, have 10 outlet openings in the area of the armpits as well as in the area of the arm joints 12, i.e. on the inner side of the joints, and finally in the front area of the sleeves on the side facing the inner side 13 of the forearm of the wearer. Specifically from the area of the inner arm 13 of the forearm, a lot of heat can be dissipated because the blood circulates there in arteries, veins and vessels that run close to the skin surface. In the lower part of the body, gas outlets are arranged in the area of the hollows of the knees 7, and furthermore at the end of the gas duct which leads along the buttocks to the area of crotch 8, where an outlet opening is likewise arranged. The highest pressure in the gas duct system is in the section before the gas reaches a first outlet opening, i.e. in the ring that surrounds the hip. After each passing of an outlet opening, the gas pressure is reduced and is ultimately lowest in the inner arm areas of the forearms and in the hollows of the knees. In order for the cooling gas or cooling air to be distributed as desired, the outlet openings toward the outer ends of the branching gas duct system must always become slightly larger to account for the pressure drop. The outlet opening has the smallest size in the area of the lower back because the pressure in the gas duct system is still greatest there, and the outlet openings are larger in the area of the forearms. As a result, the pressure drop can be compensated for so that depending on the size and design of the outlet openings approximately the same amount of gas or air can flow out everywhere per time. The outlet openings can be formed as slots or fine perforations in the gas ducts 4-6.

In one variant, the gas duct system can be divided into a number of separate gas ducts for certain outlet openings or each of them so that the gas pressure in each duct is equal and each outlet opening can be operated at the same pressure. In this case, however, each separate gas duct must be supplied separately with pressurized gas from the pressurized gas cylinder. Each hose can then also be equipped with a separate valve so that each outlet opening can be operated with adjustable pressure.

In a further variant, the suit can also be manufactured as a two-piece suit consisting of trousers and jacket, made from a textile material. The branching gas ducts can then be connected via an additional hose coupling between trousers and jacket. Both items of clothing, i.e. jacket and trousers, can also be equipped with such a cooling system independently of each other, i.e. one for the trousers with its own supply hose and one for the jacket likewise with its own supply hose.

As described above, the gas ducts are attached on the inner side of the outer layer of the suit 1. The suit is equipped with an inner lining covering these gas ducts 3-6 so that only the inner lining is in contact with the body of the wearer. This is made of a textile material that is well tolerated by the skin, is breathable and also absorbs sweat, for example pure cotton or cotton with only a small fraction of synthetic fibers. A cotton inner lining makes the suit comfortable to wear and furthermore such an inner lining can be flowed through by the gas flowing from the outlet openings and this then freely finds its way to the outside along the body and suit and finally flows outwardly mainly at the sleeve openings, at the neck as well as at the lower ends of the trouser legs.

Figure 3:
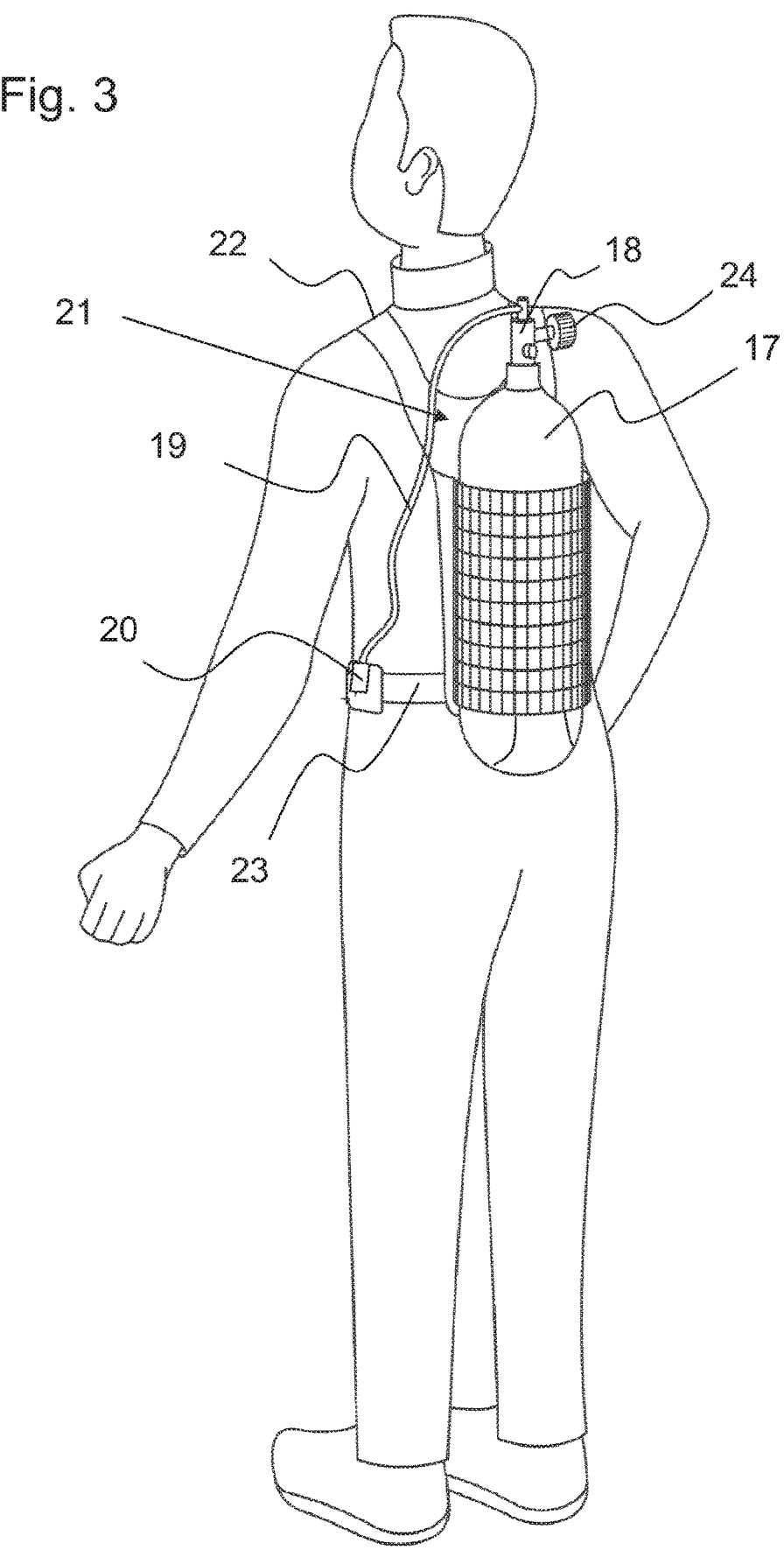
FIG. 3: the wearer of the cooling suit seen diagonally from behind, carrying a pressurized gas cylinder in a carrying device on the back, and the hose connection to the gas ducts in the suit.

FIG. 3 shows the wearer of the cooling suit as seen diagonally from behind. He or she carries a pressurized gas cylinder 17 in a carrying device 21 on his or her back. This cylinder 17 contains for example 3 kg of pressurized air or another suitable dry gas, for example nitrogen, at a pressure of 300 bar. This means that this cylinder 17 and its pressurized air content form an energy storage device, and it is precisely this energy that is used to efficiently cool the body of the wearer. The dosed outflow of the pressurized gas or pressurized air lets it be adiabatically expanded during outflow. The energy stored in the form of pressure is dissipated to the environment in the form of heat, whereby the gas or the air is significantly cooled. The completely passively cooled air, or correspondingly the cooling gas, then flows via the hose coupling 20 into the gas duct system of the suit and gradually exits through various outlet openings in this gas duct system. The air or gas absorbs heat from the body of the wearer or cools it in physiologically tolerable and finely adjustable level at the points in question. The cooling by natural convection is supported by the system and sweat on the surface of the body of the wearer is absorbed by the air or gas permanently streaming past and is eventually transported outward via the breathable fabric of the inner lining.

The pressurized gas cylinder 17 is equipped with a valve 18, which can be opened to several snap-in positions by means of a setting wheel 24. Depending on the degree of valve opening 18, more or less pressurized gas per time flows out of the pressurized gas cylinder 17. The more pressure gas is released, the greater the cooling effect in the suit, but the shorter the duration of use. With a pressurized gas cylinder with a volume of 2 liters and, for example, air at a pressure of 300 bar, 600 liters of air can be carried along. A pressure cylinder with a volume of 3 liters at 600 bar even contains 900 liters of compressed air. In the lowest opening position, approx. 1 liter of air per minute constantly flows from the cylinder so that a maximum discharge time of 10 hours is achieved. At a higher cooling capacity, up to 20 liters of air per minute can be drawn from the cylinder, wherein the cooling time is reduced to 30 minutes. A rapid cooling function allows the release of 40 liters of air or gas per minute. In this mode, a body can be intensively cooled for 15 minutes if, for example, it needs to be used near a source of fire.

The wearer can adjust the cooling capacity to a comfortable level at any time by adjusting the valve 18. It is clear that this valve 18 having setting wheel 24 can also be arranged somewhere other than directly on cylinder 17, for example on a belt worn with the suit, or at the front of the carrying device 12 so that the setting wheel 24 is within reach and also visible. In this case, a hose from cylinder 17 leads to the valve 24 and from the valve to the hose sleeve 2. Furthermore, the pressure cylinder 17 can optionally be equipped with a manometer, which allows conclusions to be drawn about the current contents of the cylinder so that one always knows how long one still has an intact cooling function. It goes without saying that the minimum and maximum cooling time depends on the gas content of the pressurized gas and the pressure prevailing therein. A pressure cylinder with a capacity of 2 liters or more of gas or air content offers even longer cooling times.

In order to carry around as little weight as possible, the pressurized gas cylinder 17 is preferably made of lightweight material, for example based on carbon-reinforced fibers, and provided with an airtight coating. Such cylinders are commercially usual. Furthermore, the pressurized gas cylinder 17 can be used in a customized carrier device 21, with which it can be carried along very comfortably on the back. For this purpose, the support device is equipped with two wide shoulder carrying straps 22 and a lap strap 23. With this carrier device 21, the wearer can also bend down effortlessly, or can kneel down and lie on the side to carry out work. The device is compact and light-weight and does not interfere with the carrier's work, or hardly at all. Due to their low weight, the carrier only has to carry an additional weight of about 5 kg for the whole system but can operate in perfect body climate conditions. The suit by itself weighs about 1.5 kg. The carrier device 21 with a 2-liter pressure cylinder, for example, weighs only less than 6.5 kg in total.

If the pressurized gas cylinder or pressurized air cylinder becomes empty during an operation, it can be replaced with a full one in no time at all. For this, the hose connection to the hose sleeve 2 is released, the pressure cylinder 17 is removed from the support device 21 and a full pressure cylinder 17 is inserted. Their hose 19 is coupled to the cooling suit 1 with the hose sleeve 2 and the cooling system is again ready for use. A standard quick coupling for gas hoses, e.g. a swivel coupling for pressureless coupling, or a linear coupling is suitable as a hose coupling.

However, this cooling suit can be used not only with a pressurized cylinder carried along directly but also with pressurized air from a separate pressurized cylinder or a separate pressure container, especially when users are seated on seats and perform their tasks, such as flying or flying along in helicopters or airplanes and driving and travelling in all kinds of vehicles. Used in this way, it is suitable for use in helicopters, transport aircraft, tanks, civilian and military vehicles, ships, submarines etc., wherein the expanded pressurized air can be obtained from a provided pressure cylinder or a stationary pressure vessel. Several cooling suits can then also be connected collectively to a large pressure vessel, which can be recharged by an on-board compressor, wherein the pressure vessel can then be cooled separately and actively by a cooling device, for example to the normal internal temperature of the aircraft, vehicle or other room. This cooling suit therefore offers a tremendous relief for many members of emergency services of all kinds and significantly increases their work efficiency. However, it can also be used by any private person for any kind of work or outdoor sports activities, whenever the temperatures are high or high humidity leads to muggy weather conditions.

LIST OF NUMERALS

1 Suit
2 Hose sleeve
3 Air duct into the trouser joints
4 Air duct at the sleeves
5 Air duct in the shoulder area
6 Air duct around the hips
7 Hollows of the knees
8 Crotch
9 Abdominal area
10 Arm pit area
11 Chest area
12 Arm joint area
13 Inside of the lower arm
14 Neck area
15 Lower back area
16 Zip fastener on the combination suit
17 Pressurized air cylinder
18 Valve on the pressurized air cylinder
19 Hose starting at the pressurized air cylinder
20 Hose coupling 21 Carrier device for pressurized air cylinder
22 Carrying loops for the carrier device
23 Hip belt for carrier device
24 Adjusting wheel for pressurized air valve

What is claimed is:

1. A cooling suit having a portion for legs, for torso, and for arms, the cooling suit comprising:
an opening hose sleeve;
inwardly branching gas ducts having several outlet openings arranged in a space between an outer gas-permeable textile layer and an inner gas-permeable textile layer;
a pressurized gas cylinder with a coupling piece connected to the hose sleeve;
wherein the portion for the legs, the torso, and the arms form a one-piece suit of gas-permeable textile with the inner gas-permeable textile layer of pure cotton or cotton with a fraction of synthetic fibres, the one-piece suit being equipped with a zip fastener extending from a collar down to a crotch of the portion for the legs; and
wherein the inwardly branching gas ducts are flat textile ducts attached on an inner side of the outer gas-permeable textile layer of the one-piece suit by lamination, welding, sewing and/or stitching to the inner side of the gas-permeable textile layer,
wherein the inwardly branching gas ducts are coupled to the hose sleeve,
wherein one of the inwardly branching gas ducts leads from the hose sleeve into a ring which encloses a hip area, wherein the ring in a front area is open for opening the zip fastener, and starting from the ring, and for each of the legs, the one gas duct branches down from the hip area and is led downward on an outer side of the leg for a thigh and leads further down to a back side of the leg to finally end in an area of a hollow of a knee,
wherein a second one of the inwardly branching gas ducts, from the ring that surrounds the hip area, branches upward from an area of a lower back, and runs along a spine into another ring-shaped gas duct of the inwardly branching gas ducts, wherein the another ring-shaped gas duct surrounds a neck and throat of a wearer, whereby the another ring-shaped gas duct is open at the front area so that the zip fastener can be opened, and starting from the another ring-shaped gas duct, two sections run down the front area of the one-piece suit along the zip fastener and end in a chest area of the wearer,
wherein a third one of the inwardly branching gas ducts branches off over shoulders into sleeves of the one-piece suit, along a side of the sleeves facing an inner side of the arms of the wearer, and
wherein a fourth one of the inwardly branching gas ducts at the hip area branches off at a rear from the ring downwardly in a middle of the ring, which leads downward into a buttocks area and ends in an area of the crotch,
wherein the several outlet openings become larger from opening to opening of the several outlet openings toward an outer end of the inwardly branching gas ducts to account for a pressure drop, and wherein the several outlet openings are positioned for letting gas flow out to cool hips, the hollows of knees, the crotch, abdomen, arm joint, armpit on inside of the arm joint, chest, side directed to the torso, the neck, and lower back, and
at least one valve with an adjusting wheel is provided at the pressurized gas cylinder to be carried along for delivery of expanded gas from the pressurized gas cylinder into the inwardly branching gas ducts, wherein the pressurized gas cylinder is made of carbon-fiber material; and
a textile carrier system operable to receive the pressurized gas cylinder in the form of a backpack with two shoulder carrying straps and a lap strap to form a carrier device by which the wearer of the one-piece suit can bend down or can kneel down and lie on his or her side to carry out work, and
wherein the one-piece suit alone weighs less than 3.5274 pounds (1.6 kg), and the pressurized gas cylinder holds a volume of 2 to 5 liters for carrying from 600 liters to 1500 liters of pressurized air at a pressure of 4351.13 psi (300 bar).

2. The cooling suit according to claim 1, further comprising additional branching gas ducts for the legs and torso portions which are each separately connectable via a hose coupling to the pressurized air cylinder so that the legs and torso portions are coolable independently from each other by separate valves of the cooling suit.

3. The cooling suit according to claim 1, wherein the pressurized gas cylinder has a 2-liter maximal capacity, the cooling suit including the textile carrier system and the pressurized gas cylinder made of carbon-fiber material weighs less than 14.33 pounds (6.5 kg) in total.

* * * * *